United States Patent [19]
Abrahmsén et al.

[11] Patent Number: 5,156,959
[45] Date of Patent: Oct. 20, 1992

[54] METHOD TO EXPORT GENE PRODUCTS TO THE GROWTH MEDIUM OF GRAM NEGATIVE BACTERIA

[75] Inventors: Lars Abrahmsén, Stockholm; Tomas Moks, Taby; Björn Nilsson, Sollentuna; Mathias Uhlén, Uppsala, all of Sweden

[73] Assignee: KabiGen AB, Stockholm, Sweden

[21] Appl. No.: 602,935

[22] Filed: Oct. 24, 1990

Related U.S. Application Data

[63] Continuation of Ser. No. 941,143, Dec. 12, 1986, abandoned.

[30] Foreign Application Priority Data

Dec. 13, 1985 [SE] Sweden .................... 8505921

[51] Int. Cl.$^5$ ............... C12P 21/02; C12P 19/34; C12N 15/00; C12N 7/00
[52] U.S. Cl. .................... 435/69.1; 435/91; 435/172.3; 435/235.1; 435/320.1; 435/252.3; 435/252.33; 536/27; 530/350; 935/9; 935/27; 935/31; 935/48; 935/56; 935/58; 935/61; 935/72; 935/73
[58] Field of Search .............. 435/69.1, 91, 172.1, 435/235, 252.3, 252.33, 320.1, 172.3; 536/27; 530/350; 935/9, 27, 31, 48, 56, 58, 61, 72, 73

[56] References Cited

U.S. PATENT DOCUMENTS

| | | | |
|---|---|---|---|
| 4,338,397 | 7/1982 | Gilbert et al. | 435/68 |
| 4,472,302 | 9/1984 | Karkhanis | 260/112 R |
| 4,624,922 | 11/1986 | Horikoshi et al. | 435/172.3 |

OTHER PUBLICATIONS

Char et al., J. Biol. Chem. vol. 260, pp. 8925–8935 (1985).
Nilsson et al., Embo vol. 4, pp. 1075–1080 (1985).
Kudo et al., J. Bacteriology, vol. 156 pp. 949–951 (1983).
Kobayashi et al., J. Bacteriology, vol. 165 pp. 728–732 (1986).
Pugsley et al., Embo, J. vol. 3 pp. 2393–2397 (1984).
Uhlin et al., Gene vol. 6 3 pp. 91–106 (1978).
Rao et al., Gene vol. 3 pp. 247–263 (1978).
Gilleland, H. E. et al., J. Bacteriol. vol. 125, pp. 267–281 (1976).
Colbert, D. et al., J. of Biol. Response Modifers vol. 3 pp. 255–259 (1984).
Abrahamsen et al., "Analysis of Signals for Secretion in the Staphylococcal Protein A Gene", The EMBO Journal, vol. 4, No. 1.
PCT Publication Number WO 84/00774 (abstract).

(List continued on next page.)

Primary Examiner—Joan Ellis
Attorney, Agent, or Firm—Burns, Doane, Swecker & Mathis

[57] ABSTRACT

A process for expressing proteins in Gram(−) bacteria and providing for extracellular secretion thereof, comprising the steps: a) introducing into a Gram(−) bacterium a recombinant DNA construction comprising a promoter, a signal sequence enabling translocation and processing, and a structural gene encoding the desired protein to be expressed; b) cultivating the bacterium under conditions resulting in filamentous growth; and c) recovering the extracellularly secreted protein; a recombinant DNA construction comprising:
  a promoter, a signal sequence and a structural gene including a cleavage region,
  wherein the structural gene is of the formula:

$$(E)_n(B)_m\text{-}Y,$$

where n is an integer $\geq 1$, m is an integer, Y is a DNA sequence encoding a desired protein and E and B are the genes corresponding to the protein A regions E and B, with the proviso that the structural gene is different from that encoding natural protein A;
  a plasmid vector comprising such recombinant DNA construction;
  a Gram)−) bacterium harbouring said recombinant DNA construction; and
  proteins obtained by such process.

25 Claims, 4 Drawing Sheets

OTHER PUBLICATIONS

"Secretion of heterologous gene products to the culture medium of *Escherichia coli*", *Nucleic Acids Research*, Lars Abrahmsen, et al., vol. 14, No. 18 (1986), pp.7487-7500.

"Expression of Human Insulin-Like Growth Factor I in Bacteria: Use of Optimized Gene Fusion Vectors To Facilitate Protein Purification",*Biochemistry*, Tomas Moks, et al., vol. 26, No. 17 (1987), pp. 5239-5244.

"Dual expression system for generation, analysis and purification of antibodies to a repeated sequence of the *Plasmodium falciparum* antigen Pf155/RESA", by Stefan Stahl, et al., Department of Biochemistry and Biotechnology, Royal Institute of Technology, S-10044 Stockholm, Sweden.

"Analysis and Use of the serum Albumin Binding Domains of Streptococcal Protein G", Journal of Molecular Recognition, Per-Ake Nygren, et al., vol. 1, No. 2 (1988), pp.69-74.

"Differential stability of recombinant human insulin--like growth factor II in *Escherichia coli and Staphylococcus aureus*", Bjorn Hammarberg, et al., Department of Biochemistry and Biotechnology, Royal Institute of Technology, S-10044 Stockholm, Sweden.

"Analysis of the leaky phenotype of *Escherichia coli* induced by the expression of staphylococcal protein A", Lars Abrahmsen, et al., Department of Biochemistry and Biotechnology, Royal Institute of Technology, S-10044 Stockholm, Sweden.

"Extracellular production of cloned α-amylase by *Excherichia coli*", Gene, Ilari Suominen, et al., vol. 61 (1987), pp. 165-176.

Asp.Pro.Gly.Asn.Ser.Arg.Gly.Ser.Val.Asp.Leu.Gln.Pro.Ser.
GAT CCG GGG AAT TCC CGG GGA TCC GTC GAC CTG CAG CCA AGC TT
     EcoRI  SmaI   BamHI  SalI  PstI      HindIII

Fig. 3

```
  -1 +1
  Ala.Ala.Glu.Phe.Pro.Gly.Ile.Arg.Arg.Pro.Ala.Ala.Lys.Leu.
  GCT GCG CAA TTC CCG GCG ATC CGT CGA CCT GCA GCC AAG CTT     pAS1
          EcoRI       BamHI  SalI    PstI    HindIII
              SmaI
  -1 +1
  Ala.Ala.Arg.Ile.Pro.Gly.Asp.Pro.Ser.Thr.Cys.Ser.Gln.Ala.
  GCT GCC CGA ATT CCC CGG GAT CCG TCG ACC TGC AGC CAA GCT T   pAS2
          EcoRI       BamHI  SalI    PstI    HindIII
              SmaI
  -1 +1
  Ala.Ala.Pro.Asn.Ser.Arg.Gly.Ser.Val.Asp.Leu.Gln.Pro.Ser.
  GCT GCC CCG AAT TCC CGG GGA TCC GTC GAC CTG CAG CCA AGC TT  pAS3
          EcoRI       BamHI  SalI    PstI    HindIII
              SmaI
```

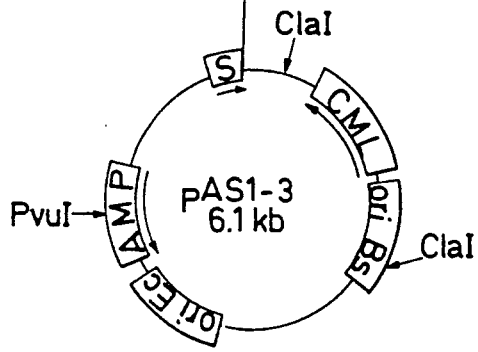

```
  +59
  Ala.Glu.Phe.Pro.Gly.Ile.Arg.Arg.Pro.Ala.Ala.Lys.Leu.
  GCG GAA TTC CCG GCG ATC CGT CGA CCT GCA GCC AAG CTT     pASE1
      EcoRI       BamHI  SalI    PstI    HindIII
          SmaI
  +59
  Ala.Arg.Ile.Pro.Gly.Asp.Pro.Ser.Thr.Cys.Ser.Gln.Ala.
  GCC CGA ATT CCC GGG GAT CCG TCG ACC TCG AGC CAA GCT T   pASE2
      EcoRI       BamHI  SalI    PstI    HindIII
          SmaI
  +59
  Ala.Pro.Asn.Ser.Arg.Gly.Ser.Val.Asp.Leu.Gln.Pro.Ser.
  GCC CCG AAT TCC CGG GGA TCC GTC GAC CTG CAG CCA AGC TT
      EcoRI       BamHI  SalI    PstI           pASE3
          SmaI                           HindIII
```

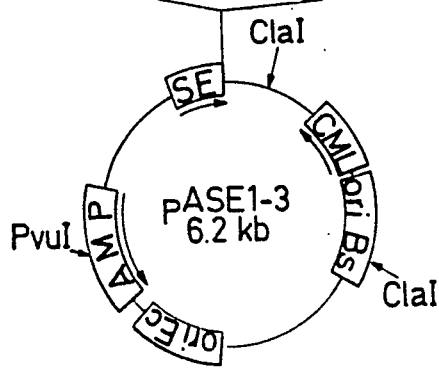

```
              1         10        20        30        40
                                              ↓
pASEB   MKKKNIYSIRKLGVGIASVTLGTLLISGGVTPAANAAQHDEAQQNAFYQVLN
                                              └──→ Domain E ↓       ↓
pASB-1  MKKKNIYSIRKLGVGIASVTLGTLLISGGVTPAANAARIRADNKFNKEQQNAF
                                                   └──→ Domain B ↓
pASB-2  MKKKNIYSIRKLGVGIASVTLGTLLISGGVTPAANAAPNSADNKFNKEQQNAF
                                                   └──→ Domain B
```

Fig. 8

IGF-1    229 BASES

```
  1 EcoRI    11        21        31        41        51
GAATTCTAACGGTCCCGAAACTCTGTGCGGTGCTGAACTGGTTGACGCTCTGCAGTTT
  AsnSerAsnGlyProGluThrLeuCysGlyAlaGluLeuValAspAlaLeuGlnPhe
            └─▶insulin growth factor I
 59        69        79        89        99        109
GTTTGCGGTGACCGTGGTTTTTATTTTAACAAACCCACTGGTTATGGTTCTTCTTCTCGT
ValCysGlyAspArgGlyPheTyrPheAsnLysProThrGlyTyrGlySerSerSerArg 119       129       139       149       159       169
CGTGCTCCCCAGACTGGTATTGTTGACGAATGCTGCTTTCGTTCTTGCGACCTGCGTCGT
ArgAlaProGlnThrGlyIleValAspGluCysCysPheArgSerCysAspLeuArgArg 179       189       199       209       219 HindIII 229
CTGGAAATGTATTGCGCTCCCCTGAAACCCGCTAAATCTGCTTAGAAGCTT
LeuGluMetTyrCysAlaProLeuLysProAlaLysSerAla***
```

Fig. 9

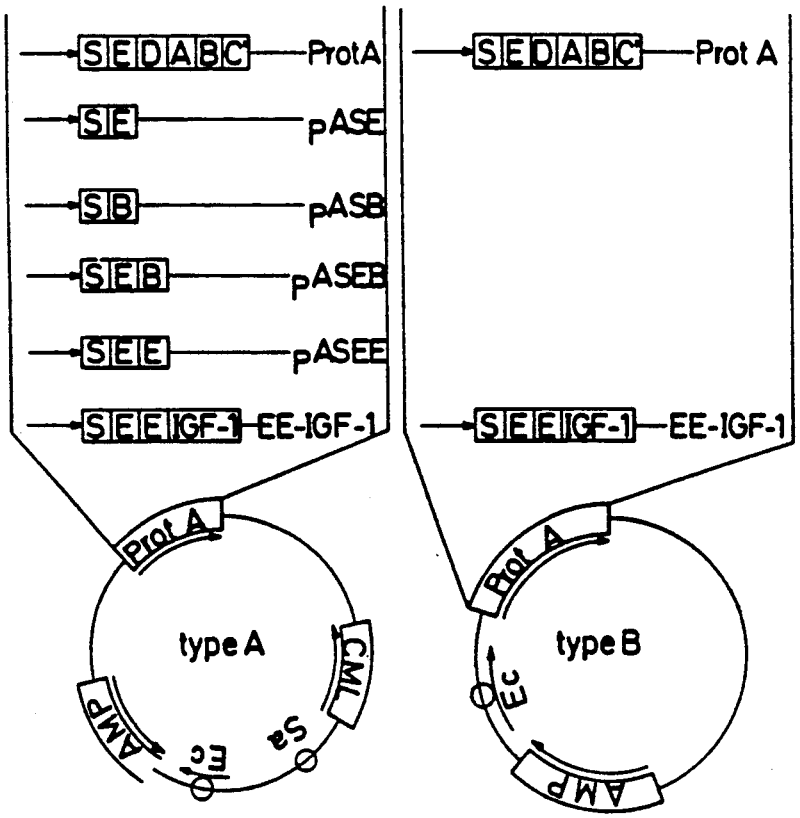

METHOD TO EXPORT GENE PRODUCTS TO THE GROWTH MEDIUM OF GRAM NEGATIVE BACTERIA

This application is a continuation of application Ser. No. 06/941,143, filed Dec. 12, 1986, now abandoned.

BACKGROUND OF THE INVENTION

1. Field of the Invention

This invention relates to the use of recombinant-DNA technology and the use of Gram negative bacteria such as *Escherichia coli* (hereinafter called *E.coli*) to express and export gene products to the growth media of such organisms.

Thus, the invention provides for a process for expressing proteins in Gram negative bacteria to provide for extracellular secretion thereof. The invention furthermore provides for a recombinant DNA construct and plasmid vectors and Gram negative bacteria comprising such recombinant DNA construction. The invention also extends to proteins obtained by the process of the invention.

2. Description of the Related Art

The relatively new recombinant DNA technology, whereby novel recombinant DNA structures may be constructed and introduced into a prokaryotic or eukaryotic host cell, has made it theoretically possible to produce a great number of proteins. The use of bacteria to produce heterologous gene products has made it possible to obtain proteins which can otherwise only be obtained from natural sources at a considerable cost. Well known examples of polypeptides originally from humans produced in bacteria are human Growth Hormone (hGH), insulin, α-interferon, γ-interferon, somatostatin and somatomedins (Insulin-like Growth Factors).

The use of bacteria to express foreign genes have faced many practical and biological problems including stability of the polypeptide due to proteolysis, level of expression, precipitation of the protein product correlated to misfolding and lack of biological activity of the protein after purification. To solve these problems a variety of techniques have been developed to be able to use the well characterized entero bacteria *E.coli* to express any gene product. These methods include the use of different promoters to be able to regulate the level of expression, gene fusions to stabilize normally unstable proteins in the cell and the use of signal peptides to translocate proteins out from the cytoplasm to the periplasmic space in where disulphide bridges can be formed in contrast to the cytoplasm where the reducing environment makes this formation difficult. Proteins with cystein bridges in the structure expressed in the cytoplasm of *E.coli* will usually not get the correct tertiary structure due to the difficulties associated with forming these bridges. This could potentially lead to precipitation of the polypeptide upon overproduction, a rapid proteolytic degradation if not precipitated in the cell and no biological activity of the expressed and purified polypeptide. This has been observed in *E.coli* for expression of proinsulin, insulin A-chain, insulin B-chain, Insulin-like Growth Factors and tissue specific Plasminogen Activator (t-PA). To overcome this problem the polypeptide has to be renatured after purification or secreted to the periplasmic space of *E.coli* where the correct folding can be potentially achieved. One other aspect of bacterial gene expression and secretion apart from folding and stability is the use of Gram positive bacteria. These organisms have a different organization of the membrane structures surrounding the cell cytoplasm compared to the Gram negative counterpart. The Gram positive prokaryotes have only one cell membrane and secreted proteins get exported to the growth medium where secretion in the Gram negative *E.coli* locates the protein to the periplasmic space due to a double membrane layer surrounding the cell cytoplasm. By using Gram positive bacteria, secreted gene products can be collected from the growth media which would facilitate the downstream processing of the product. The emphasis to use Gram positive bacteria in industrial processes is thus correlated to this secretory process, but from other aspects it would be preferred to use the well characterized *E.coli* in large scale production of gene products simply because expression systems are more developed for this organism.

SUMMARY OF THE INVENTION

The present invention provides a solution to the limitations in the application of the use of *E.coli* in industrial processes. This invention permits gene products to be secreted from *E.coli* to the growth medium quantitatively. This genetic approach to get export of a protein in Gram negative bacteria is based on induction of filamentous growth where the expression of the desired gene product is dependent on the heat shock response and this response gives a leakage of periplasmic located proteins to the growth medium quantitatively. The basis of this invention will be explained below.

DESCRIPTION OF THE PREFERRED EMBODIMENTS

It is well known that signal peptides are present in the N-terminus of expressed proteins that are to be secreted across a membrane both in prokaryotic and eukaryotic cells. This signal peptide, consisting of 20–40 amino acids, is cleaved off during the translocational process. It is known that many protein factors are correlated to this secretory process but the molecular mechanism is not known in absolute detail even though good models exist which are resonably adjacent to reality.

The present invention will be illustrated below with reference to staphylococcal protein A. This protein is known as a cell wall component of the pathogenic bacteria *Staphylococcus aureus*, hereinafter called *S. aureus*, and it is well known for its specific binding to the constant region of certain classes of antibodies from most mammals including man. Protein A is also known to be highly repetitive in its structure and 5 regions of approximately 58 amino acids in each region situated in a tandem repeat are all individually functional as binding to immunoglobulins (such as human IgG). At the DNA level it was shown that a signal sequence, responsible for the translocation of protein A out from the cytoplasm, is present prior to these five IgG binding regions. This signal sequence has been shown to be functional also in *E. coli* and protein A is thus found in the periplasmic space after introduction of the protein A gene.

In the research underlying this invention fragment B of protein A was placed immediately after the signal sequence resulting in blocked secretion. The obvious conclusion is that the differences in amino acid sequence between fragment B and E are important for the secretory process. The *E. coli* cells expressing this fragment B of protein A are grow filamentously due to incomplete cell division. This has eariler been observed for *E. coli* expressed proteins that are precipitating in the cell. Now we found that proteins located in the periplasmic space, like β-lactamase, was leaking into the growth medium. When expressing fragment SE it was surprisingly found that this E fragment is almost entirely exported to the growth medium of *E. coli*. This also correlated to filamentous growth of the cells. Other fragments found to induce filamentous growth (although to a different extent) was fragment SEE and SEB. All these smaller fragments of protein A are somehow induce a defect in cell division leading to an export of periplasmic proteins to the growth medium.

When fusing SEE to a gene encoding human insulin-like growth Factor-1 (IGF-I), a growth factor consisting of 70 amino acids, resulting in SEE-IGF-I it was found that the gene product could be recovered from the growth medium. Also in this experiment a filamentous morphology of the cells could be observed.

All the above-mentioned experiments were carried out in a type A vector as shown in FIG. 9. The type A vectors are based on pRIT4 having the protein A derived gene transcription opposite to the β-lactamase (bla) gene. When placing SEE-IGF-I in a type B vector the expression level was 20–40 times higher compared to the type A orientation. The type B vector is based on pEMBL with the protein A derived gene transcription in the same direction as the β-lactamase gene (bla). The filamentous growth in these cells is very pronounced. The export to the growth medium is very efficient.

The present results show that export to the growth medium of our gene products is correlated to filamentous growth of the *E.coli* cells and also that the level of expression can be correlated to this induction.

The protein A gene consisting of SEDABC in a type A vector was grown at 30° C. or 42° C. In the higher temperature, high enough to get a heat shock response, the expression level is 20–40 times higher and the export to the growth medium is efficient.

The conclusion that can be drawn from the research leading to the present invention is that filamentous growth of *E. coli* gives an export of periplasmic proteins to the growth medium. Filamentous growth is induced in *E. coli* cells harboring the protein A promoter and signal sequence and due to the orientation of the fragments in the plasmid vector or due to the size of the part of protein A expressed we get different levels of export to the growth medium of the periplasmic proteins.

The basic concept of this invention constitutes a major advance in the art as induction of filamentous growth in *E. coli* leads to high expression and efficient secretion when placed after the protein A signal sequence and promoter.

It is to be noted that this invention is not dependent upon a biological explanation for the observations in the behavior of this expression-secretion system.

Although the invention is not limited to any specific theory, we have, however, a reasonable explanation for the observations made.

The protein A gene is a heat shock gene itself in *E. coli*. This means that protein A should be induced of heat shock. The reason for this phenomenon is found upstream of the earlier reported *E. coli*-like promoter in the protein A gene where a sigma-32-like promoter is found. This suggested sigma-32 promoter sequence is homologous to the consensus sequence suggested for the heat shock genes. The sigma-32 factor, responsible for the heat shock response, transcribes 17 different genes in *E. coli*.

Heat shock response is triggered when the *E. coli* cell is stressed. It has been suggested that improperly folded proteins are the main triggering effect and this induction could be carried out by heat, 4% EtOH, oxidative agents, chemicals causing misreading or production of foreign proteins not able to get a proper tertiary structure.

In our case small fragments of protein A or a high production of a larger fragment triggers the heat shock response. When this response is triggered, the protein A gene will be transcribed even more, leading to a more pronounced triggering. This heat shock response is also gives defects in the cell division, viz. so called filamentous growth. In this disclosure it is shown that also this type of growth gives an export of the periplasmic product to the growth medium.

By growing an *E. coli* strain having the protein A gene in an A type vector at 30° C. or 42° C. it is shown herein that this temperature induction gives high expression and export, which is supports the biological explanation and gives an excellent induction system. This means that the strain can be grown at low temperature producing at a low level and after the cell mass has been created the temperature is shifted to 42° C. whereafter the production of the product takes place and the product is also secreted.

Heat shock response is also triggers an ATP dependent protease designated La. Therefore the production would preferentially take place in a strain deficient in the La protease.

Accordingly, the present invention provides for a process for expressing proteins in Gram negative bacteria and providing for extracellular secretion thereof said process comprising the steps:

a) introducing into a Gram (−) bacterium a recombinant DNA construct comprising a promoter, a signal sequence enabling translocation and processing, and a structural gene encoding the desired protein to be expressed;

b) cultivating the bacterium under conditions resulting in filamentous growth; and c) recovering the extracellularly secreted protein. In such process the expression of the desired protein is preferably under the same transcriptional control as that of the filamentous growth. In one embodiment of the process of the invention the transcriptional control is based on induction of htpR expressing the Sigma-32 protein factor.

As previously indicated the concept of this invention is based upon growing Gram negative bacteria under conditions resulting in filamentous growth. Such filamentous growth may be due to the character of the recombinant DNA construction and the protein expressed therefrom. The filamentous growth may also be due to external induction or a combination of both. Thus, filamentous growth may be caused by increased temperature in cultivation to induce heat shock response, but it may also be caused by introducing into the cultivating medium 9 denaturating agent, such as ethanol.

Due to the fact that the protein expressed in a host cell by a recombinant DNA construct as defined above will be recognized by the cell as foreign or improperly folded, this may induce a heat-shock response in the bacterium.

The recombinant DNA construct can be introduced into the bacterium in different ways. Thus, it can be introduced into the chromosomal DNA of the bacterium or it can be introduced by being contained in a plasmid vector.

In a preferred embodiment of the process of the invention the recombinant DNA construct contains as a single sequence that of protein A. It is preferred that the structural gene adjacent to the signal sequence contains a cleavage region encoding the N-terminal amino acid residues of the mature protein to be recovered. Such cleavage region may be constituted so as to code for at least six amino acid residues. Said residues are preferably: Ala Gln His Asp Glu Ala.

In the process of the invention the structural gene may comprise genes selected from the E, EE and EB domains of protein A. The structural gene may also comprise a production gene, such as that encoding the insulin like growth factor 1 (IGF-1).

The invention also provides for a recombinant DNA construct comprising:
  a promoter, a signal sequence and a structural gene including a cleavage region,
wherein the structural gene is of the formula:

$(E)_n(B)_m$-Y, where n is an integer $\geq 1$, m is an integer, Y is a DNA sequence encoding a desired protein and E and B are the genes corresponding to the protein A regions E and B excluding the structural gene from that encoding natural protein A. In such construction n may be one and m may be zero, n may also be two and m may be zero. As a specific embodiment n and m may both be one.

As a preferred embodiment of the invention the recombinant DNA construction is one wherein n is two, m is zero and Y is the gene encoding IGF-1 or IGF-2.

The invention also includes plasmid vectors comprising the recombinant DNA construction as defined above. Such plasmid vector may be one originating from pEMBL9.

According to another aspect of the invention it covers a Gram negative bacteria containing such recombinant DNA construct either harbouring such construction in its chromosome or harbouring a plasmid vector containing same. A preferred bacterium to use in this invention is an E.coli, such as E.coli HB101.

According to yet another aspect of the invention there are also provided proteins prepared while using the concept of this invention.

The present invention will now be further illustrated by specific examples with reference to the appended drawings, wherein:

BRIEF DESCRIPTION OF THE DRAWINGS

FIG. 3 shows the different pAS and pASE vectors constructed as described in section I. CML is the chloramphenicol acyl transferase gene, ori $B_s$ is the origin of replication for B. subtilis and S.aureus, ori Ec is the origin of replication for E.coli, AMP is the $\beta$-lactamase gene, S is the signal sequence and E is the E region from protein A.

FIG. 8 shows the nucleotide sequence of the synthetic IGF-I gene. The EcoRI site and the HindIII site flanking the synthetic fragment is shown as well as the deduced amino acid sequence.

FIG. 9 shows the two types of plasmid vectors used to express the different protein A derived constructs. CML is the chloramphenicol acyl transferase gene, S.a. is the origin of replication for S. aureus, Ec is the origin of replication for E.coli, AMP is the $\beta$-lactamase gene and Prot A refers to the different protein A constructs as shown in the linear illustrations.

Figure 1:
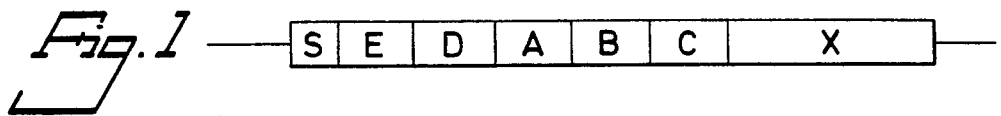
FIG. 1 is a schematic illustration of the protein A gene indicating its different coding regions. S is the signal sequence, A-E are the IgG-binding regions and X is the C-terminal part which lacks IgG-binding activity.

The invention will in the following be further illustrated by specific examples, which, however, must not be considered to limit the invention in any way. The examples show the application of the system applied to a synthetic gene encoding human insulinlike growth factor I (IGF-I) and fused to SEE to form SEE-IGF-I. It was found that this protein also was secreted in the same manner as the small portions of the protein A gene, and in a type B vector the level of expression was very high.

The vector pASEE has been deposited with the Deutsche Sammlung von Mikroorganismen (DSM), Göttingen, Federal Republic of Germany, under deposit number 3593 in an E.coli RR1$\Delta$M15.

Starting Materials

Bacterial hosts:

Two different strains of E.coli K12 were used in the Examples: HB 101 (Boyer, H. W. et al J.Mol.Biol., 41, 459–472 (1969)) and JM 103 (Messing, J. Methods Enzymol., 101, 20–79 (1983)). (the strains are available at the Department of Biochemistry and Biotechnology, Royal Institute of Technology, Stockholm, Sweden).

Cloning vehicles:

The cloning vehicles used in Examples were pBR322 (Bolival, F. et al, Gene 2,93–113 (1977)), pEMBL8 (Dente et al, Nucl.Acids Res. 11, 1645 (1983)), pEMBL 9 (Dente et al, Nucl.Acids Res. 11, 1645 (1983)), pRIT4 (Nilsson, B. et al, EMBO J. 4, 1075 (1985)), pSPA 11 (Uhlén, M. et al, Gene 23, 369 (1983)) and pSPA 16 (Uhlén, M. et al, J.Bacteriol., 159, 713 (1984)). The synthetic gene encoding IGF-I has been described elsewhere (Elmblad, A. et al, in Third European Congress on Biotechnology III, 287-296, Verlag Chemie, Weinheim (1984)). The plasmid vector pASEE constructed in Examples has been deposited with the Deutsche Sammlung von Mikroorganismen (DSM), Göttingen, Federal Republic of Germany, under No. DSM.

Buffers and Media

Coating buffer:
1.59 g $Na_2CO_3$, 2.93 g $NaHCO_3$ and 0.2 g $NaN_3$, made up to 1 liter with distilled $H_2O$ PBST:
8.0 g NaCl, 0.2 g $KH_2PO_4$, 2.9 g $Na_2HPO_4 \times 12H_2O$, 0.2 g KCl, 0.2 ml Tween ®20 and 0.2 g $NaN_3$ made up to 1 liter with distilled $H_2O$ (pH 7.4).

TSB:
30 g Tryptic Soy Broth, made up to 1 liter and autoclaved.

TBAB:
30 g Tryptic Blood Agar Base, made up to 1 liter and autoclaved.

ONPG-buffer:
2 mM o-Nitrophenyl-$\beta$-D-galactoside (ONPG, Sigma product No N-1127) in 0.1M potassium phosphate buffer, pH 7.3, containing 15 mM 2-mercaptoethanol and 1 mM $MgCl_2$.

Routine Methods

Certain procedures were carried out repeatedly in the Examples. Unless otherwise specified, they were done exactly as follows each time they were carried out.

Methods used routinely in molecular biology are not described (like the use of commercial restriction enzymes, DNA-ligations, Bal 31 exonuclease, S1 nuclease and Klenow polymerase)

Transformations:
Transformation of E.coli K12 with plasmid DNA was performed exactly as described (Morrison, D.A., Methods in Enzymology, Academic Press 68, 326-331 (1979)). The transformants were selected in a conventional manner on plates (TBAB) containing 70 mg/l ampicillin.

Isolation of plasmid DNA:
Plasmid DNA was isolated as described by Birnboim, H.C. et al, Nucl.Acids Res. 7, 1513 (1979). Small scale preparations to screen a large number of transformants were made exactly as described by Kieser, T. Plasmid 12, 19-36 (1984).

Sepharose 6B chromatography:
Plasmid DNA to be used for Bal 31 pr S1 treatment were run on a Sepharose 6B gel filtration in a 10 mM Tris, 1 mM EDTA and 500 mM NaCl-buffer. In this way DNA is separated from RNA.

Elution of DNA fragments:
Elution of DNA fragments from either agarose or polyacrylamide gel pieces were performed exactly as described by Maxam et al, P.N.A.S. (USA), 74, 560-564 (1977).

DNA sequencing:
DNA sequence analysis was performed exactly as described by Sanger, F. et al J.Mol.Biol., 143, 161 (1980)

Detection and quantification of protein A:

An ELISA test (Enzyme linked immunosorbent assay) was used to quantify protein A. The test makes use of special microtiter plate (Titertek, Amstelstad, Netherlands) having no net charge. The wells are coated with human IgG (Kabi AB, Sweden) in a coating buffer. Test samples are added and protein A is bound to the Fc portions of the IgG adsorbed in the well. Protein A is then assayed by an anti-protein A (from rabbit) conjugated to $\beta$-galactosidase (from Pharmacia AB, Uppsala, Sweden).

Assay:
The wells of a microtiter plate are filled with 75 $\mu$l of a solution of human IgG at 16 ng/ml in Coating Buffer and the plate is incubated at room temperature for at least 1 hour. The wells are washed three times with 100 $\mu$l PBST and 50 $\mu$l of sample is added to each well. For quantitative determination 2 fold dilutions are made. After incubation for 1 hour the wells are washed 3 times with 100 $\mu$l PBST followed by addition of 50 $\mu$l anti-protein A-$\beta$-galactosidase (the amount of protein A binding capacity added to each well corresponds to the molar amount of IgG added to each well as detected by titration with protein A in excess). After incubation for 45 minutes, the wells were washed 3 times with 100 $\mu$l PBST followed by addition of 125 $\mu$l ONPG buffer. After incubation for 20-30 minutes 150 $\mu$l 0.1M NaOH was added to stop the reaction. The quantification is made by running a 2-fold dilution of a protein A standard solution of known concentration in parallel with the 2-fold dilutions of the test samples. The absorbance at 405 nm is measured for each well by a photometer.

$\beta$-galactosidase assay:
Quantification of $\beta$-galactosidase was assayed by a colorimetric procedure using o-nitrophenyl-$\beta$-D-galactoside (ONPG, Sigma product No N-1127) as substrate as described by Miller, J. H. (Experiments in Molecular Genetics, Cold Spring Harbor, N.Y.; Cold Spring Harbor Laboratory, 1972). The reaction was followed by a spetrophotometer at 405 nm.

$\beta$-lactamase assay:
The amount of $\beta$-lactamase activity was determined spectraphotometrically exactly as described by O'Callaghan et al, Antimicrob.Agents Chemother, 57 (1968).

Osmotic shock:
The periplasmic located proteins were released by an osmotic shock exactly as described by Nossal et al, J. Biol.Chem. 241, 3055 (1965).

EXAMPLES

I Analyses of the protein A nucleotide sequence

The protein A gene comprises on IgG binding region (domains E,D,A,B,C) and one cell wall attached region (region X) (FIG. 1). These two regions are preceded by a signal sequence.

In order to make fusion vectors containing fusion points after the signal sequence and after region E, respectively, it is desirable to know the nucleotide sequence around the fusion point.

The nucleotide sequence of protein A is known (Uhlén, M. et al, J. Biol. Chem. 259, 1695-1702 (1984)). The full disclosure of this reference is incorporated herein by reference.

In the fusion point after the signal sequence (hereinafter called S) there is an Mst I restriction enzyme site. After region E there is also an Mst I restriction enzyme site. By digesting the protein A gene in an appropriate plasmid vector with Mst I, followed by insertion of linkers, general usable vectors can be obtained, as will be described in the following.

II Construction of pAS, pASE and pASEE

In the following step is described the construction of plasmid vectors where unique EcoRI sites is placed after S and SE respectively. There is also described how SEE is constructed containing an EcoRI site between the EF regions as well as after the SEE construct.

A. Construction of pAS, pASE and pASEE plasmid vectors

50 μg of pRIT4 (Nilsson, B. et al, EMBO J., 4, 1075 (1985)) (FIG. 2) was partially digested with Mst I using 5U of restriction enzyme incubated for 2 h at 37° C. After incubation at 65° C. for 30 minutes the reaction mixture was divided into three separate reactions. EcoRI-linkers of different length were added to each reaction respectively. To tube one an 8-mer linker was added (GGAATTCC), to tube two a 10-mer linker was added (CCGAA TTCGG) and to tube three a 12-mer linker was added (CCCGAATTCGGG). After ligation (as described in Routine Methods), the ligation mixtures were digested with EcoRI, respectively, followed by a dilution to 2 μg/ml and ligation. Transformation was performed as described in Routine Methods and ampicillin resistant transformants were selected. In each reaction two main types of vectors were found. One type contains the signal sequence followed by the EcoRI linker and the mp9 multilinker. The other type of vector contains the EcoRI linker after region E followed by the mp9 linker. By the addition of EcoRI at different lengths the mp9 linker restriction sites are available in the three reading frames for each type of construct (FIG. 3).

Apart from these two types of vectors shown in FIG. 3 in the experiment containing the 12-mer EcoRI linker one more type of plasmid vector could be recovered. This construct contains SE-12-mer linker-E-mp9 linker. In this way 4 amino acids are introduced between the two E regions as well as an EcoRI restriction site. This vector was designated pASEE and has the mp9 linker in the type 3 reading frame (FIG. 3). All constructs have been confirmed over the linker regions using DNA sequencing.

III. Construction of B gene fragments

The following experiment describes subcloning of a gene fragment coding for region B of staphylococcal protein A.

Figure 4:
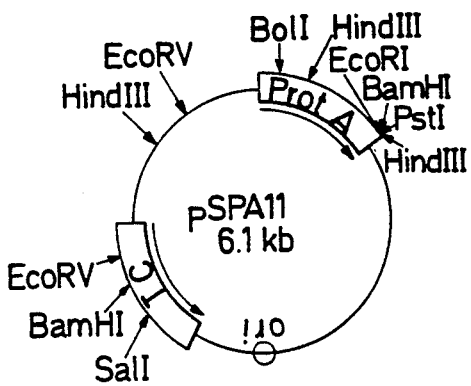
FIG. 4 shows a plasmid vector harboring the protein A gene followed by a multirestriction enzyme linker. Prot A is the gene encoding the IgG binding region of protein A. TC is the gene encoding tetracycline resistance and ori is the origin of replication in E.coli.
Figures 5, 6, 7:
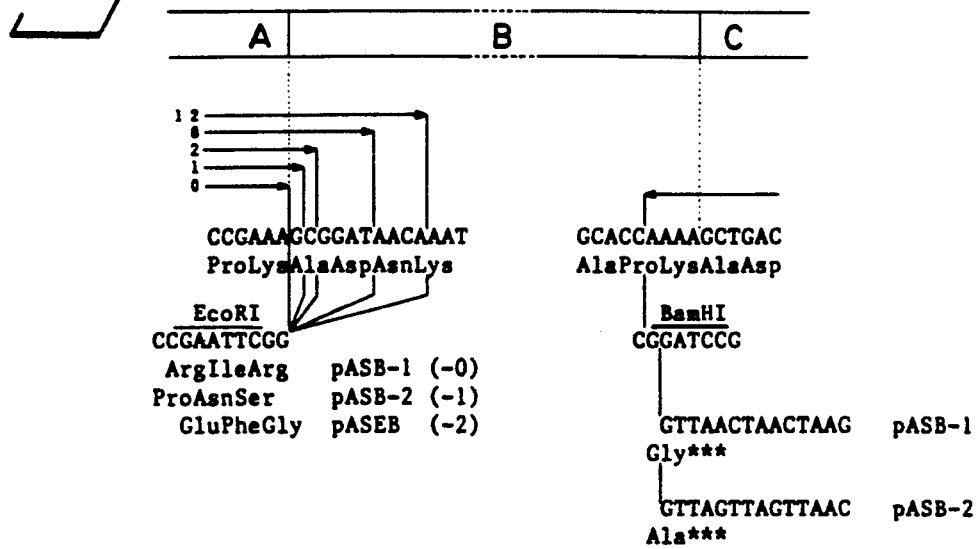
FIG. 5 shows the different gene fragments encoding the B region of protein A. The arrows to the left represent the different Bal 31 clones obtained. The EcoRI linker attached to the different Bal 31 constructs is shown. The amino acid sequences over the EcoRI site into the B region for the B-0, B-1 and B-2 construct is shown. To the right is shown the position of the BamHI linker in the 3' end of the B fragment. It is also shown the translational stops of the stop linker (FIG. 6) in the two possible orientations.
FIG. 6 shows the stop-linker creating an immediate translational stop independent of the orientation of the stop linker. The three different reading frames for each orientation shown.
FIG. 7 shows the amino acid sequence of the junction between the signal peptide and the different pASB constructs compared to the junction in native protein A. The arrows over each amino acid sequence show the position of processing as analyzed by amino acid sequencing of expressed fragments from E. coli HB101.

The starting material, the plasmid vector pSPA11, has the protein A gene down to a Sau3 AI restriction site situated in region C 117 base pairs downstream from region B. After purification of pSPA11, the purified plasmid was run on a Sepharose 6B column in order to get the plasmid pure from RNA which serves as a competitive inhibitor in the Bal31 treatment. About 100 μg of the purified pSPA11 (FIG. 4) was digested with EcoRI cleaving 117 base pairs downstream from region B. Exonuclease Bal 31 was used as described in Routine Methods. After Bal 31 digestion the reaction mixture was precipitated with EtOH followed by treatment with 10U Klenow polymerase in the presence of 0.5 mM dNTPs to ensure blunt ends. The pool of DNA of heterologous lengths were ligated with BamHI 8-mer linkers (CGGATCCG). After ligation the reaction mixture was cleaved with BamHI and Hind III. The Hind III site is situated 79 base pairs upstream of region B. The reaction mixture was run on a 5% polyacrylamide gel electrophoresis to separate fragments of heterologus lengths. The fragments around 250 base pairs were cut out from the gel and electroeluted and ligated to pEMBL9 previously cleaved with Bam HI and Hind III. After transformation to E.coli JM103 white colonies were selected on TBAB plates containing X-gal and IPTG. A clone with four nucleotides removed from region B was chosen for further work (FIG. 5).

Plasmid DNA from this clone was purified and run on a Sepharose 6B to remove RNA. About 100 μg plasmid DNA was further digested with Hind III and treated with exonuclease Bal 31 as described in Routine Methods. After treatment with Klenow polymerase (10U) in the presence of 0.5 mM dNTP for 30 minutes at 37° C. to ensure blunt end, the reaction mixture was ligated to EcoRI 10-mer linkers (CCGAATTCGG). After digestion with EcoRI and Bam HI the DNA was loaded to a 5% polyacrylamide gel electrophoresis. Slices around the desired length of 179 base pairs were cut out and electroeluted. The DNA isolated from the elution was ligated to pEMBL9 digested with EcoRI and Bam HI. After transformation to E.coli JM103 white colonies were selected on TBAB plates containing X-gal and IPTG. Sequences analysis revealed three clones of interest (referred to as 0, −1 and −2 respectively) were selected for work. The FIGS. (0, −1 and −2) describes the number of nucleotides digested into region B prior to the attachement of the EcoRI linker as shown in FIG. 5.

The three clones of the three different reading frames into region B (hereinafter called B-0, B-1 and B-2) were cleaved with Bam HI. The sticky end of the Bam HI was removed with S1-nuclease as described in Routine Methods. The translational stop linker shown in FIG. 6 was ligated to each reaction mixture. The lysine residue in each construct will now be replaced with either a Gly or Ala dependent on the orientation of the incoming stop linker as shown in FIG. 6. After transformation into E.coli JM103 sequence analysis of isolated clones containing the B fragments having the stop linker attached downstream. The sequence analysis revealed that B-0 is ended by a Gly residue, B-1 with an Ala residue and B-2 with an Ala residue.

These fragments are now to be cloned into some of the vectors described in I.

IV. Construction of pASEB, pASB2 and pASB2

The fragment of B was now to be cloned into pAS and pASE.

About 50 μg of the vectors having B-0, B-1 and B-2 and the stop linker were cleaved with EcoRI and Hind III respectively. Hind III cleaves directly after the stop linker. The B fragment from each vector was isolated using polyacrylamide gel eletrophoresis.

The B-0 fragment was ligated to pAS2 (FIG. 3) cleaved with EcoRI and Hind III. After transformation to E.coli HB101 and restriction analysis of plasmid DNA from individual clones the pASB-1 plasmid vector could be isolated having fragment B of protein A after the signal sequence.

The B-1 fragment was ligated to pAS3 (FIG. 3) cleaved with EcoRI and Hind III. After transformation to E.coli HB101 and restriction analysis of plasmid DNA from individual clones the pASB-2 plasmid vector could be isolated having fragment B of protein A after the signal sequence.

The difference between pASB-1 and pASB-2 is the three amino acids present in the EcoRI linker region as shown in FIG. 7.

The B-2 fragment was ligated to pASE1 (FIG. 3) cleaved with EcoRI and Hind III. After transformation to E.coli HB101 and restriction analysis of plasmid DNA from individual clones the pASEB plasmid vector could be isolated having fragment of protein A attached to region E.

V. Construction of pASEE-IGF-I

In this experiment is shown how a synthetic gene encoding human insulinlike growth factor I (IGF-I) was cloned into the pASEE vector described in section I.

The synthetic gene encoding IGF-I (FIG. 8) (Elmblad, A. et al, in Third European Congress on Biotechnology III, 287–296, Verlag Chemie, Weinheim (1984)) was cleaved out from pUC8 with EcoRI and Hind III. The gene fragment encoding IGF-I was isolated by polyacrylamide gel electrophoresis followed by electroelution.

The plasmid vector pASEE was partially cleaved with EcoRI and linearized vector was isolated from 1% agarose gel electrophoresis. After electroelution the linear vector was digested with Hind III and subsequently isolated by 1% agarose gel electrophoresis. The IGF-I fragment was ligated to this pASEE vector and after transformation pASEE-IGF-I could be isolated in a background of pASE-IGFI. pASEE-IGFI is encoding after the signal sequence an EE fused to IGF-I.

VI. Construction of pE8EE-IGF-I

In this section is shown how SEE-IGF-I is cloned in the other orientation of pEMBL compared to the pAS vectors described in section I.

About 50 μg of pASEE-IGF-I (as described in section V) was cleaved with TaqI and Hind III. The restriction endonuclease TaqI cleaves 179 basepairs upstream from the translational start of the protein A gene and HindIII cleaves downstream of the IGF-I gene. The reaction mixture was run on a 4% polyacrylamide gel electrophoresis and the SEEIGF-I fragment was cut out and electroeluted.

This fragment was ligated to pEMBL8 cleaved with AccI and HindIII. After transformation to E.coli HB101 the plasmid pE8EE-IGF-I could be isolated as analyzed by restriction analysis.

VII. Construction of pE9EDABC

In this section is shown how SEDABC is cloned into pEMBL9 in order to get the IgG binding portion of protein A in the reverse orientation.

The plasmid vector pRIT4 was cleaved with TaqI and EcoRI. The restriction endonuclease TaqI cleaves 179 basepairs upstream from the TTG start codon and EcoRI cleaves in region C of protein A.

This fragment was ligated to pEMBL9 cleaved with AccI and EcoRI. After transformation to E.coli HB 101 the plasmid vector pE9EDABC could be isolated. This plasmid has the protein A gene oriented from the origin of replication.

VIII. Expression and localization of protein A derived fragments in E.coli

Different protein A constructs were grown overnight and expression levels and localization of protein A, β-galactosidase (intracellular marker) and β-lactamase (periplasmic space marker) were measured. The plasmid pASEE was transformed to E.coli HB101 in order to be hosted in the same E.coli strain as the other constructs. After overnight growth the cells were centrifuged. The cells were treated with an osmotic shock followed by centrifugation (as described in Routine Methods). The spheroplasts in the pellet were sonicated to release the intracellular proteins.

Type of vector (A or B) refers to the orientation of the protein A derived construct compared to the β-lactamase (AMP) gene. (FIG. 9). Assay methods of β-galatosidase, β-lactamase and protein A were performed as described in Routine Methods.

The results from the experiments can be seen in table 1.

It can be seen that small fragments of protein A induces filamentous growth as well as leakage of the periplasmic located proteins including the protein A derived fragment.

In the gene constructs containing region B directly after the signal sequence (pASB1 and pASB2) the major portion of protein A fragment is found in the intracellular fraction. The conclusion is that this behavior is due to inability of the leader peptidase to cleave off the signal peptide and the translated B peptide gets stuck to the cytoplasmic membrane.

N-terminal sequencing (by conventional Edman degradation technique) of the B fragments purified from E.coli cultures harboring the pASB1 and pASB2 plasmids respectively revealed processing sites into the signal sequence confirming that the leader peptidase does not cleave off the signal peptide (FIG. 7). In addition enhanced levels of expression are seen from these constructs, filamentous growth as well as leakage to the extracellular compartment of the normally periplasmic proteins.

The pASEE-IGF-I construct also gives an extracellular hybrid protein, also correlated with filamentous growth.

The two constructs representing a type B vector (pE8EE-IGF-I and pE8EDABC) give the most pronounced filamentous growth.

It is noteworthy that the pE8EDABC expressed in E.coli HB101 gives a high expression level as well as secretion while pRIT4 gives a low expression. It could be argued that this enhanced expression is dependent on the upstream lac-promoter in the pE9EDABC construct. It was however shown that this filamentous growth and expression level is independent of addition of IPTG (known to induce transcription from the lac-promoter).

What can be concluded from this section is that different constructs based on the protein A promoter and signal sequence induce filamentous growth, export of periplasmic proteins to the growth medium and enhanced expression from the protein A constructs.

As filamentous growth is correlated with heat shock response in E.coli the next experiment was carried out to see if the high expression from the protein A promoter is due to heat shock response, or if a high expression for unknown reasons gives a heat-shock response.

IX. Expression of pRIT4 in HB101 with and without a heat shock

Figure 2:
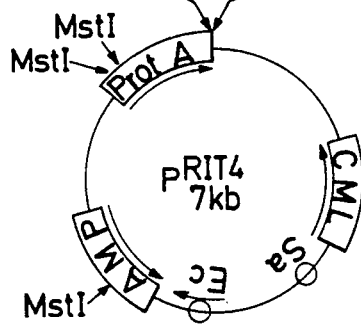
FIG. 2 illustrates the plasmid vector pRIT4 including the protein A gene. The mp 9 multirestriction enzyme linker is shown with its actual reading frame relevant for gene fusions. CML is the chloramphenicol acyl transferase gene, Sa is the origin of replication for S.aureus, Ec is the origin of replication for E.coli, AMP is the $\beta$-lactamase gene and Prot A represents the IgG binding portion of the protein A gene.

The plasmid pRIT4 harbors the IgG binding portion of protein A in a type A vector (FIG. 2, FIG. 9 and section VIII). When growing an E.coli HB101 overnight protein A is poorly secreted (9%) to the growth medium. This protein A construct was chosen to be grown with and without a heat shock via an increase in temperature even though 4% EtOH and different oxidative agents are well known alternative ways to elicit a heat shock response.

using other bacterial host cells as well. Moreover, other signal sequences than those originating from protein A can be used.

TABLE 1

| Plasmid | Orientation | Filamentous growth | Level of expression (mg/liter) | Intracell (%) lac bla spa | | Medium (%) lac bla spa |
| --- | --- | --- | --- | --- | --- | --- |
| pBR322 | — | — | ND | 93 3 ND | 1 94 ND | 1 3 ND |
| pSPA16 | — | (—) | 3 | 99 3 2 | 1 83 88 | 1 14 10 |
| pASB1 | A | ++ | 27 | 97 4 89 | 1 66 6 | 2 30 5 |
| pASB2 | A | + | 8 | 92 4 52 | 1 41 5 | 7 55 43 |
| pASEB | A | + | 33 | 96 4 8 | 1 50 37 | 3 46 55 |
| pASE | A | + | 0.2 | ND ND 1 | ND ND 5 | ND ND 94 |
| pASEE | A | + | 33 | ND ND 1 | ND ND 24 | ND ND 75 |
| pASEE-IGF-I | A | + | 31 | ND ND 2 | ND ND 21 | ND ND 77 |
| pE8EE-IGF-I | B | ++ | 61 | ND ND 2 | ND ND 13 | ND ND 85 |
| pRIT4 | A | (—) | 2 | ND ND 2 | ND ND 89 | ND ND 9 |
| pE8EDABC | B | ++ | 41 | ND ND 3 | ND ND 28 | ND ND 69 |

ND = not detected

E.coli HB101 harboring pRIT4 was grown overnight (30° C.). The overnight culture was inoculated (150 μl) to 15 ml fresh TSB media containing 70 μg/ml ampicillin and the cells were grown for 2.5 h in two separate shake flasks.

One of the cultures was diluted with 15 ml TSB (30° C.) and incubated at 30° C. To the other flask was added 15 ml TSB at 54° C. and the flask was incubated at 42° C.

After 3 hours incubation from the time point of the switch the cells were centrifuged. The cell pellet was washed once with 10 ml PBST and resuspended in 5 ml PBST and sonicated for 3×30 seconds (in a MSE sonicator, microtip, powerlevel 6). After centrifugation at 16,000 g for 10 minutes the supernatant was collected.

Protein A was quantified both in the media and in the sonicated fraction which corresponds to the total amount in the periplasm and cytoplasm.

The results are:

| Plasmid | Temperature | OD580 nm | Level of (mg/l) expression | Filamentous growth | % extracellular |
| --- | --- | --- | --- | --- | --- |
| pRIT4 | 30° C. → 30° C. | 0.210 | 0.16 | (—) | 13 |
| pRIT4 | 30° C. → 42° C. | 0.289 | 3.14 | + | 68 |

The relatively low expression is verified by the low Optical Density ($OD_{580}$). The expression level in the heat-shocked cell culture is enhanced twenty fold.

This can only be explained if the transcriptional control of the protein A gene itself is that of the heat shock response.

Although the invention has been exemplified herein using only a few specific genes it is to be understood that the basic concept of this invention can be applied to genes expressing any desired gene. Thus, in addition to expressing for example IGF-I the invention can be used for the production of other proteins, such as other medicinally useful proteins, for example other somatomedins, such as IGF-II, Nerve Growth Factor (NGF), Epidermal Growth Factor (EGF), and Platelet Derived Growth Factor (PDGF). The technique of the invention can also be used for production of alpha-, beta- and gamma-interferons, interleucines, insulin, neuropeptides, gastrointestinal peptides or other peptides of interest.

It is further to be observed that the invention is not limited the use of E.coli as a host cell but can be applied

We claim:

1. A recombinant DNA construct comprising: a Staphylococcus protein A promoter, and a signal sequence operatively linked to a structural gene wherein the structural gene has the formula:

$$(E)_n(B)_m-Y,$$

where n is 1 or 2, m is 0 or 1, Y is a DNA sequence encoding a heterologous protein and E and B are the genes corresponding to the protein A regions E and B, with the proviso that the structural gene is different from that encoding natural protein A.

2. A recombinant DNA construct according to claim 1, wherein n is 1 and m is zero.

3. A recombinant DNA construct according to claim 1, wherein n is 2 and m is zero.

4. A recombinant DNA construct according to claim 1, wherein n is 1 and m is 1.

5. A recombinant DNA construct according to claim 1, wherein n is 2, m is 0 and Y is the gene encoding IGF-1 or IGF-2.

6. A recombinant DNA construct according to claim 1, wherein the signal sequence encodes the amino acid residues Ala Gln His Asp Glu Ala.

7. A vector comprising the recombinant DNA construct of claim 1.

8. The vector of claim 7 wherein said vector is pEMBL9.

9. A Gram negative bacteria transformed with the recombinant DNA construct of claim 1.

10. The Gram negative bacteria of claim 9 wherein said bacteria is E. coli.

11. The Gram negative bacteria of claim 10, wherein said bacteria is E. coli HB101.

12. The Gram negative bacteria of claim 9 wherein said construct integrates into the chromosome of said bacteria.

13. A process for expressing a heterologous protein in Gram negative bacteria and providing for extracellular secretion thereof from viable bacteria, said process comprising
   (a) transforming a Gram negative bacteria with a recombinant DNA vector comprising a Staphylococcus protein A promoter and a signal sequence operatively linked to a structural gene encoding a heterologous protein wherein the structural gene is of the formula: $(E)_n(B)_m-Y$, wherein n is 1 or 2, m is 0 or 1, Y is a DNA sequence encoding a heterologous protein and E and B are the genes corresponding to the protein A region E and B, with the proviso that the structural gene is different from that encoding natural protein A;

(b) cultivating said bacteria under conditions to induce growth of the transformed Gram negative bacteria;

(c) expressing said heterologous protein; and (d) recovering the extracellularly secreted protein encoded by the gene.

14. The process according to claim 13 wherein the expressed protein is recognized as foreign or not folded properly and induces a lon-response in the bacteria.

15. The process according to claim 13 wherein the Gram negative bacteria is subjected to an external stimulus.

16. The process according to claim 15 wherein the external stimulus is increased cultivation temperature to induce heat shock.

17. The process according to claim 16 wherein the external stimulus is the use of a denaturing agent in the culture medium.

18. The process according to claim 13 wherein the recombinant DNA vector integrates into the chromosomal DNA of the bacteria.

19. The process according to claim 13 wherein the structural gene adjacent to the 3' end of the signal sequence contains a DNA segment encoding a cleavage region enabling cleavage of the signal peptide.

20. The process according to claim 19 wherein said amino acids are: Ala Gln His Asp Glu Ala.

21. The process according to claim 19 wherein the structural gene formula is selected from the group consisting of n=1, m=0; n=2, m=0; and n=1, m=1.

22. A process according to claim 21, wherein the heterologous gene is the gene encoding the insulin like growth factor 1(IGF-1).

23. A process for expressing a heterologoup protein in *E. coli* and providing for extracellular secretion thereof, said process comprising (a) transforming *E. coli* with a recombinant DNA vector comprising the Staphylococcus protein A promoter and signal sequence directly linked to the E and B regions of the protein A gene fused to a structural gene encoding a heterologous protein;

(b) cultivating said *E. coli* under suitable growth conditions at 30° C. or 40° C.

(c) expressing said heterologous protein; and (d) recovering the extracellularly secreted protein encoded by the gene.

24. A process for expressing a heterologous protein in a Gram negative bacteria and providing for extracellular secretion thereof, said process comprising (a) transforming Gram negative bacteria with a recombinant DNA vector comprising a Staphylococcus protein A promoter and a signal sequence operatively linked to a structural gene encoding a heterologous protein comprising the E and B regions of the protein A gene;

(b) culturing said Gram negative bacteria under conditions to induce growth of said bacteria and expression of said heterologous protein;

(c) subjecting said bacteria to heat shock conditions; and (d) recovering the extracellularly secreted protein encoded by the gene.

25. A process for expressing a heterologous protein in a Gram negation bacteria and providing for extracellular secretion thereof from viable bacteria, said process comprising (a) transforming Gram negative bacteria with a recombinant DNA vector comprising the Staphylococcus protein A promoter and a signal sequence operatively linked to a structural gene wherein the structural gene has the formula $(E)_n (B)_m$-Y, wherein n is 1 or 2, m is 0 or 1, Y is a DNA sequence encoding a heterologous gene and E and B are genes corresponding to the protein A regions E and B with the proviso that the structural gene is different from that encoding natural protein A;

(b) culturing said Gram negative bacteria under conditions to induce growth of said bacteria and expression of said heterologous protein;

(c) subjecting said bacteria to heat shock conditions; and (d) recovering the extracellularly secreted protein encoded by the gene.

* * * * *